US006988518B2

(12) United States Patent
Rackers

(10) Patent No.: US 6,988,518 B2
(45) Date of Patent: Jan. 24, 2006

(54) ROBOTIC SYSTEM AND METHOD FOR TRANSPORT OF MATERIALS WITH MINIMIZATION OF FOOTPRINT SIZE

(75) Inventor: Kevin J. Rackers, Summerfield, NC (US)

(73) Assignee: Automation Techniques, Inc., Greensboro, NC (US)

( * ) Notice: Subject to any disclaimer, the term of this patent is extended or adjusted under 35 U.S.C. 154(b) by 0 days.

(21) Appl. No.: 10/858,700

(22) Filed: Jun. 2, 2004

(65) Prior Publication Data

US 2005/0268987 A1 Dec. 8, 2005

(51) Int. Cl.
*G01N 35/04* (2006.01)
(52) U.S. Cl. .................. 141/130; 422/100; 73/864.25; 141/1
(58) Field of Classification Search .................... 141/1, 141/130; 422/65, 67, 100; 73/864.11, 864.16, 73/864.17, 864.24, 864.25
See application file for complete search history.

(56) References Cited

U.S. PATENT DOCUMENTS

| | | | |
|---|---|---|---|
| 3,576,605 A | 4/1971 | Drake et al. ................... 23/259 |
| 3,687,632 A | 8/1972 | Natelson ....................... 23/259 |
| 3,772,154 A | 11/1973 | Isenberg et al. ....... 195/103.5 R |
| 4,555,957 A | 12/1985 | Frankel et al. ............ 73/864.14 |
| 4,873,875 A | 10/1989 | Cork ......................... 73/863.01 |
| 5,772,962 A | 6/1998 | Uchida et al. ................. 422/67 |
| 6,234,033 B1 | 5/2001 | Eipel ........................ 73/864.25 |
| 6,324,114 B1 | 11/2001 | Himeno .................. 365/230.03 |
| 6,325,114 B1 * | 12/2001 | Bevirt et al. ................ 141/130 |

2002/0176801 A1 11/2002 Giebeler et al. ......... 422/82.05

OTHER PUBLICATIONS

Genesis RSP™, www.tecan.com.
VPrep™, www.velocity11.com/products/vprep/product.info.html, Aug. 25, 2004.
MICROLAB® 4000 Reliable High Performance Workstations, www.hamiltoncompany.com.
HTC PAL Options, Compact High Throughput LC Sample Injection System, CTC Analytics AG.
NEBULA™ Series Systems, Unipoint™ Software, Cyberlab C-400, C-250, and C-230 Automated Plate Preparation Workstations, www.wilson.com.
Cellular Assay Workstation for High-Throughput Toxicity Testing.

* cited by examiner

*Primary Examiner*—David J. Walczak
*Assistant Examiner*—Peter deVore
(74) *Attorney, Agent, or Firm*—Withrow & Terranova, PLLC

(57) ABSTRACT

A robotic system and method that provides three axes of movement to couple a robotic arm with a desired target for movement of materials, including but not limited to fluids. The robotic arm moves in two axes of direction only, and the targets move in the third axis of direction to couple the robotic arm with the desired target. The targets are contained on trays that are controlled to move linearly to accomplish the third axis of movement. Multiple trays each containing targets are provided and are vertically stacked on top of each other to increase the target handling capacity of the robotic system without increasing the footprint size of the robotic system. Each axis of motion is accomplished by control of an actuator by a control system and associated motion controller.

19 Claims, 13 Drawing Sheets

|  |  | $X_1$ (60A) | $X_2$ (60B) | $X_3$ (60C) | $X_4$ (60D) | $Y_1$ (40) | $Z_1$ (44) | $Z_2$ (46) |
|---|---|---|---|---|---|---|---|---|
| HOME | 0 | 0 | 0 | 0 | 0 | 0 | 0 | 0 |
| SHELF $X_1$ (50A) COLUMN 1 (71) | 1 | 50 | 0 | 0 | 0 | 100 | 20 | 0 |
|  | 2 | 50 | 0 | 0 | 0 | 100 | 30 | 0 |
|  | 3 | 50 | 0 | 0 | 0 | 100 | 20 | 0 |
|  | 4 | 0 | 0 | 0 | 0 | 100 | 20 | 0 |
| SHELF $X_3$ (50C) COLUMN 1 (71) | 5 | 0 | 0 | 50 | 0 | 100 | 20 | 0 |
|  | 6 | 0 | 0 | 50 | 0 | 100 | 310 | 0 |
|  | 7 | 0 | 0 | 50 | 0 | 100 | 300 | 0 |
|  | 8 | 0 | 0 | 0 | 0 | 100 | 300 | 0 |
| TIP WASH (72) | 9 | 0 | 0 | 0 | 0 | 32 | 415 | 0 |
|  | 10 | 0 | 0 | 0 | 0 | 100 | 0 | 0 |
| SHELF $X_1$ (50A) COLUMN 2 | 11 | 50+$\Delta C_1$ | 0 | 0 | 0 | 100 | 20 | 0 |

*FIG. 4*

ROBOTIC SYSTEM AND METHOD FOR TRANSPORT OF MATERIALS WITH MINIMIZATION OF FOOTPRINT SIZE

FIELD OF THE INVENTION

A robotic system and method for transfer of materials in three axes of motion wherein the footprint size of the robotic system is minimized.

BACKGROUND OF THE INVENTION

Robotic systems are commonly used to automate activities that would otherwise require human labor. Robotic systems include manipulators that are designed to move materials, parts, tools or specialized devices through various programmed motions for the performance of a desired task. The manipulators are typically designed to move in different axes of motion to accomplish transport of materials.

Because many robotic systems need to accomplish a wide range of movement in different axes of motion, designers of robotic systems have to design in enough space in the robotic system in order for manipulators to accomplish their full range of movement. This space is often much greater than the space needed to contain the materials being transported so that the manipulators have enough space to access and move the materials. It is also a goal of robotic system designers to provide systems that can transport a greater amount of materials so that less robotic systems are required to transport a given amount of materials. Because of limited manufacturing space, purchasers of robotic systems scrutinize the footprint size consumed by a robotic system when making purchasing decisions. The width and depth size of a footprint is typically more important to minimize than height size for facilities employing robotic systems.

One common application for a robotic system involves fluid transfer. An example of a robotic fluid transfer system is the "Genesis RSP"™ robotic system manufactured by Tecan Instruments. A brochure illustrating and describing the Genesis RSP™ is located at http://www.tecan.com/index/com-pr-in/com-pr-in-ro__li__entry-3/com-pr-in-ro__li-genesis__rsp.htm. A copy of this brochure is contained with the Information Disclosure Statement submitted with this application on its filing date.

The Genesis RSP™ provides multiple trays containing targets located side-by-side whereby fluid from one tray is transported to another tray. Fluid transfer is accomplished by a robotic arm located above the trays moving to couple a pipette attached to the robotic arm to the desired target. The footprint size of the robotic system is larger to accommodate all of the multiple target trays. Further, the robotic arm must be designed to move in all three axes of motion to couple the pipette with the individual desired target.

Another example of a robotic fluid transfer system is described in U.S. Pat. No. 4,555,957 (hereinafter "'957 patent"). The '957 patent is similar to the Genesis RSP™ system, except that the '957 patent moves the targets on the trays in one axis of direction so that the robotic arm only need move in two other axes of direction to accomplish a three-axis robotic system.

As illustrated in FIG. 1 of the '957 patent, a horizontal translatable table (10) is provided that supports two trays (78) arranged on each side of a pipette assembly (36), wherein each tray contains targets (84) for fluid transfer. Fluid from a target on one tray is moved to a target on the other tray. The horizontal transfer table (10) is mounted on hardened guide rods (14) by means of slide bearings (16). In order for fluid transfer to occur, a stepper motor (18) drives the table (10) back and forth to move the trays containing the targets in the x-axis direction to place the desired target underneath a pipette (36) on the pipette assembly. The pipette assembly can be moved in the y-axis and z-axis directions to place the pipette over top of the target on a tray for transport of fluid. In this manner, the targets, by movement of the trays, are moved to accomplish movement in a first axis, and the pipette assembly moves in the other two axes of movement to accomplish a three-axis movement robotic system.

As can be seen from FIG. 1 of the '957 patent, the footprint width size of the robotic system must be at least the length of two trays. Further, the system is only capable of transporting materials from one tray to another tray and thus, the system's target handling capacity is limited by the amount of targets that can be contained on one tray. If more targets need to be provided for fluid transfer than can be contained on a tray, another robotic system will be required. Further, if the tray size is expanded to provide for more targets, the horizontal translatable table will also have to be increased in size thereby increasing the footprint width size of the robotic system.

Another example of a fluid transfer robotic system is the "VPrep"™ robotic system manufactured by Velocity11. A brochure illustrating and describing the VPrep™ is located at www.velocity11.com/products/vprep/product__info.html. A copy of this brochure is contained with the Information Disclosure Statement submitted with this application on its filing date.

The VPrep™ robotic system provides a plurality of trays containing targets whereby fluid from one tray is transported to another tray. The trays are located on either side of a pipette station located in the center of robotic system housing. Fluid transfer is accomplished by moving a tray horizontally from its outside resting position to a position underneath the pipette station in the center section. The tray is moved back to its resting outside position, and the fluid is transported to another tray by moving that tray to the center section underneath the pipette station.

The VPrep™ system solves the problem of a limited number of targets that can be handled like the system in the '957 patent by providing more trays so that more targets can be handled. However, the VPrep™ system does not solve the problem present in the '957 patent of having to provide a footprint width size that is the entire length of both the source target tray and the transport target tray. Further, the VPrep™ system also moves the target tray entirely and completely under the pipette station. This means that either the pipette station must provide all three axes of movement thereby adding complexity and expense since the tray is not capable of moving controllably to place the correct individual target underneath the pipette station, or the pipette station must include a number of pipettes equal to the number of targets so to that each target can be accessed without the pipette station providing a third axis of movement to select the correct target. Further, the VPrep™ system is even larger in footprint width size than the '957 patent system since an open center section must be provided between and clear of any trays to allow the pipette station to move up and down for fluid transport.

Therefore, it is desirable to provide a robotic system that provides three axes of movement in a space efficient manner whereby (1) the targets move controllably to provide one axis of movement wherein the robotic arm does not move in same axis of movement as the targets to accomplish three axes movement; (2) multiple trays are provided to increase the target handling capacity of the robotic system; and (3) the footprint size of the robotic system is minimized. The present invention accomplishes this objective in a new and novel way over prior robotic systems.

SUMMARY OF THE INVENTION

The present invention is a robotic system and method that provides three axes of movement to couple a robotic arm with a desired target for movement of materials, including but not limited to fluids. The robotic arm moves in two axes only, and the targets controllably move in a third axis orthogonal to the other two axes to couple the robotic arm with the desired target. The targets are contained on trays that are controlled to move linearly to accomplish the third axis of movement. Multiple trays each containing targets can be provided. The trays are vertically stacked on top of each other to increase the target handling capacity of the robotic system. The advantage of the present invention results in a robotic system that is smaller in size since movement of the targets provides one axis of movement thereby reducing the size needed for movement of the robotic arm. Further, since the trays are vertically stacked on top of each other, increasing the number of targets by increasing the number of trays does not result in any increase in the footprint size of the robotic system.

The robotic system comprises a control system, a frame, a plurality of first actuators attached to the frame, a plurality of linear bearings attached to the frame wherein each of the plurality of linear bearings is controlled to be moveable to any position by one corresponding actuator in the plurality of first actuators only in a first axis of motion, a plurality of shelves each containing a plurality of targets wherein each shelf in the plurality of shelves is attached to one corresponding bearing in the plurality of linear bearings and wherein each of said plurality of shelves are stacked in a vertical arrangement, and an arm attached to the frame and moveable only in two axes of motion both orthogonal to the first axis of motion. The arm comprises a second actuator that moves only in one of the two axes of motion and a third actuator that moves only in the other of the two axes of motion. The robotic system further comprises an end effector attached to the third actuator.

The control system is electronically coupled to the plurality of first actuators and second and third actuators, wherein the control system controls coupling the end effector to one of the plurality of targets by controlling an actuator in the plurality of first actuators corresponding to the shelf containing the one of the plurality of targets to independently move in the first axis of motion, and controlling the second and third actuators to move in the two axes of motion to align the end effector with one of the plurality of targets, wherein said second and third actuators are not controllable to move in the first axis of motion.

The robotic system includes a frame comprised of four sides, a top, and a base. An actuator housing is provided that houses the Z-axis actuator. The actuator housing is moveable in the Y-axis direction to provide the Y-axis direction of movement for the robotic arms of the robotic system. The actuator housing houses the Z-axis actuators that allow the robotic arm to move up and down in the Z-axis direction. In one example, the actuator housing contains two Z-axis actuators, one actuator for a robotic arm that controls the movement of an end effector housing containing one or more nozzles for fluid transfer, and one actuator for a gripper arm that is designed to grip and transport fluid containers. A control system controls movement of the actuator housing in the Y-axis direction and the robotic arms in the Z-axis direction.

The third axis of motion is accomplished by providing an X-axis actuator for each of a plurality of shelves each containing targets for transfer of materials. Multiple shelves are provided to provide handling of a greater number of targets. The shelves are vertically stacked on top of each other so that more targets can be handled by the robotic system without expanding the footprint size of the robotic system. When it is desired to transport materials to or from one of the targets on the shelves in the robotic system. The control system causes an X-axis actuator to move the particular shelf containing the target of interest in the X-axis direction, and the control system moves the end effector in the Y-axis and Z-axis direction via the Y-axis and Z-axis actuators so that the particular target on the shelf is aligned underneath the end effector. In this manner, the nozzle on the end effector can be coupled with the target(s) of interest.

The control system is comprised of a microprocessor, memory and bus communication system. The control system is coupled to a display and input keys located on the frame of the robotic system to allow an operator to program and/or configure the robotic system. The control system is also coupled to a motion controller that is coupled to the X-axis, Y-axis, and Z-axis actuators for controlling movement of the shelves containing the targets in the X-axis, and the robotic arms in the Y and Z axes. Each actuator contains an electric drive that is coupled to the motion controller via a motion controller communication control line. The microprocessor directs control of the actuators via communication with the motion controller, which in turns translates the instructions of the microprocessor into an instruction desired for an actuator.

One example of an X-axis actuator that may be used with the present invention is a linear bearing comprised of a rail attached to the inside of a side of the frame of the robotic system. Each shelf containing targets is coupled to its own dedicated rail via a rail guide. A gear rack is attached on the bottom of the shelf, and a spur gear controlled by an X-axis actuator is located underneath the shelf. The teeth of the spur gear are interlocked with the teeth of the gear rack on the bottom of the shelf. The control system causes the spur gear to rotate in either a clockwise or counterclockwise direction to move the shelf back and forth along the x-axis direction. The control system has the ability to control the shelf to move to any position so that any target on the shelf can be aligned underneath the end effector of the robotic arm. In this manner, the end effector does not have to be designed to provide a nozzle for every target on a shelf.

One example of a Z-axis actuator that may be used with the present invention comprises a lead screw that is controlled by a mechanical actuator that rotates in both the clockwise and counterclockwise direction. The robotic arm is attached to the lead screw so that rotation of the lead screw causes the robotic arm to move up and down in the Z-axis direction. The lead screw is housed inside the actuator housing. The control system is coupled to the mechanical actuator to control the rotation of the lead screw to move the robotic arm in the Z-axis direction as desired. A separate lead screw may be provided for each individual robotic arm so that each robotic arm is independently controllable to be moved in the Z-axis.

One example of a Y-axis actuator that may be used with the present invention is a belt drive system. A belt is attached on one end around a mechanical actuator that is in the form of a disc coupled to a shaft that rotates in both the clockwise and counterclockwise direction. The other end of the belt is attached to a free rotating pulley. The actuator housing is attached to the belt so that movement of the belt in the Y-axis direction also moves the actuator housing in the Y-axis direction. Since the robotic arms are attached to the actuator housing, movement of the belt provides movement of the robotic arms in the Y-axis.

Those skilled in the art will appreciate the scope of the present invention and realize additional aspects thereof after reading the following detailed description of the preferred embodiments in association with the accompanying drawing figures. One of ordinary skill in the art will recognize that the labeling of axes in the present application and association of axes with particular components of the robotic system is not meant to be limiting. The actuators of the present invention can be rearranged to provide movement of their respective components in other axes of direction, and the labeling of axes is for mere convenience of describing one example of the present invention.

BRIEF DESCRIPTION OF THE DRAWINGS

The accompanying drawing figures incorporated in and forming a part of this specification illustrate several aspects of the invention, and together with the description serve to explain the principles of the invention.

FIG. 4 illustrates a table of an example of a fluid transfer from one target on a tray to another target on another tray;

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

As an overview, the present invention is a robotic system and method that provides three axes of movement to couple a robotic arm having an end effector with a desired target for movement of materials, including but not limited to fluids. The robotic arm moves in two axes of direction only, and the targets move in the third axis of direction to couple the end effector with the desired target. The targets are contained on trays that are controlled to move linearly to any position to accomplish the third axis of movement. Multiple trays each containing targets are provided and are vertically stacked on top of each other to increase the target handling capacity of the robotic system. The advantage of the present invention results in a robotic system that is smaller in size since movement of the targets provides one axis of movement thereby reducing the size needed for movement of the robotic arm in only two axes of motion, and increasing the number of targets by increasing the number of vertically stacked trays does not result in any increase in the footprint size of the robotic system.

Figure 1:
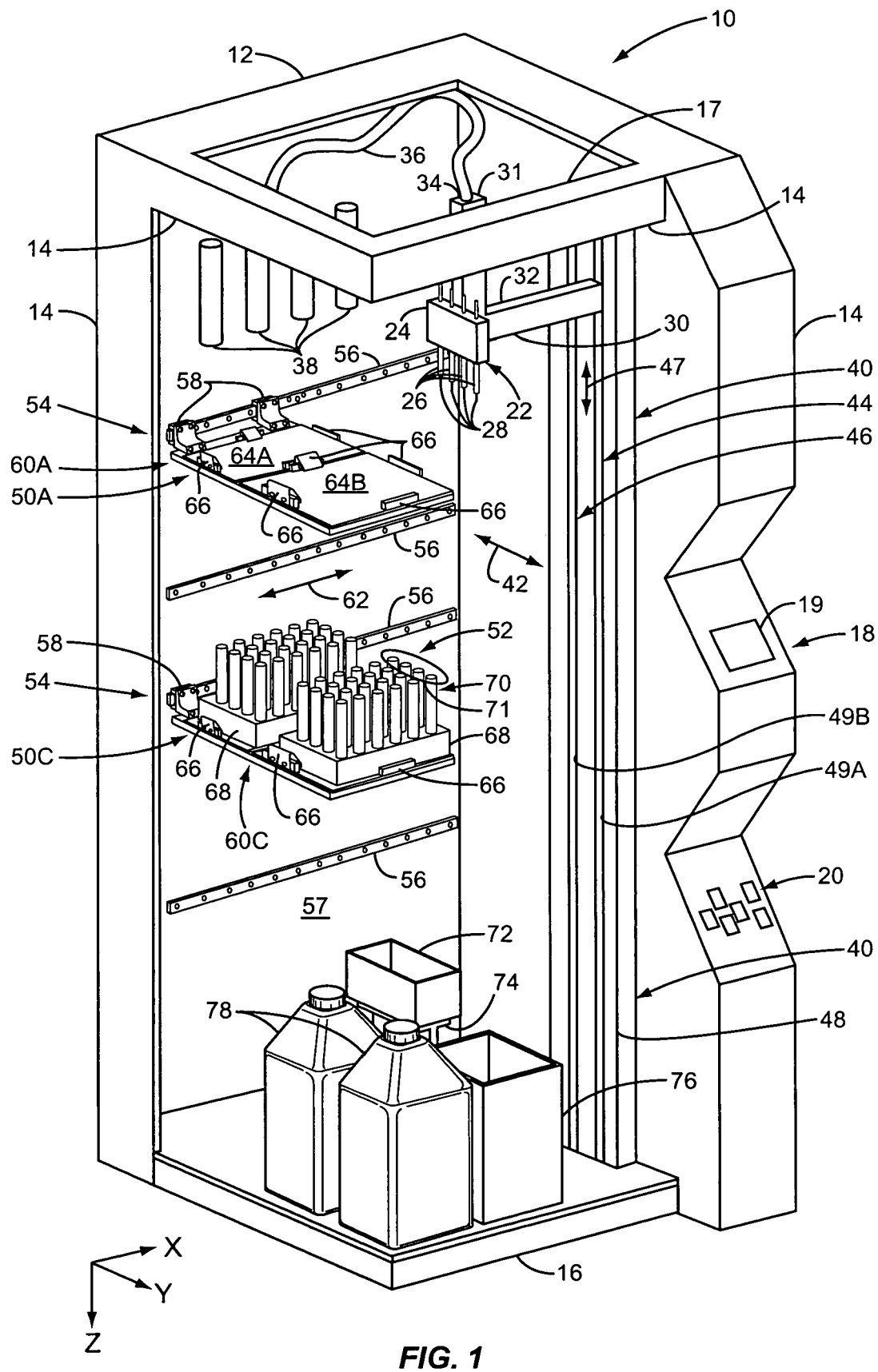
FIG. 1 illustrates an perspective view of a robotic system in accordance with the present invention.

One example of a robotic system in accordance with the present invention is illustrated in FIG. 1. The robotic system is generally designated as item 10 in FIG. 1 and the other figures in this application. The robotic system 10 is comprised of a frame 12, which consists of four sides 14, a base 16, and a top 17. The top 17 illustrated in FIG. 1 contains a rectangular orifice to allow components of the robotic system 10 to extend therethrough if needed or to provide easy access to the internal components. For example, the pumps and hose coupled to the end effector, as will be later described in this application, may reside outside of the frame 12 of the robotic system 10. However, the top 17 may also be a solid surface not containing an orifice if it is not necessary for any of the internal components of the robotic system 10 to extend therethrough or be accessed. In the example of the robotic system 10 illustrated in FIG. 1, two of the sides 14 of the robotic system 10 are solid surfaces that do not contain substantial openings or orifices, and the other two sides 14 that are closest to the viewer of FIG. 1 are substantially open for access to the internal components of the robotic system 10. A transparent door (not shown) may also be provided on the sides 14 and/or the top 17 if it is desired to allow internal access to the robotic system.

On the right-hand side of the robotic system 10 as illustrated in FIG. 1, a user interface 18 is provided for an operator to program, control, and otherwise interact with the robotic system 10. The user interface 18 is comprised of a display 19 and/or input keys or controls 20. The display 19 and input keys 20 are coupled to a control system (illustrated in FIG. 3) that controls the operation of the robotic system 10. The display 19 can display preferences in programming options, settings and/or configurations of the robotic system 10. The user can manipulate the configuration and/or programming of the robotic system 10 via the input keys 20. Alternatively or in addition to the user interface 18, the user can connect the robotic system 10 via a communication line to a remote interface located remotely from the robotic system 10 to configure and/or program the robotic system 10.

The example of the robotic system 10 illustrated in FIG. 1 is a fluid handling and transport robotic system. To this end, the robotic system 10 contains an end effector 22 that is comprised of an end effector housing 24 to transport fluids. One or more nozzles 26 are coupled to the end effector housing 24. The nozzles 26 contain nozzle tips 28 that allow for the transport of fluids via suction and dispensing as will be described below. In the example illustrated in FIG. 1, four nozzles 26 and corresponding nozzle tips 28 are provided so that fluid can be transported to/from four targets at the same time, but the robotic system 10 could contain more or less nozzles 26 and nozzle tips 28 as desired.

The end effector housing 24 is attached to a robotic arm 30 so that the control system of the robotic system 10 can control the placement of the nozzle tips 28 via its coupling to the end effector housing 24 and the robotic arm 30. Because of this coupling, movement of the robotic arm 30 moves the nozzle tips 28 accordingly. The robotic arm 30 is comprised of a vertical member 31 and a horizontal member 32. The vertical member 31 of the robotic arm 30 contains a pump connection 34 that is coupled to a pump hose 36. The other end of the pump hose 36 is coupled to one or more pumps 38 so that the nozzles 26 are each coupled to a pumping source when suction for drawing fluid from the nozzle tip 28 into the nozzle 26 is desired, as will be described later below. If it is desired for each nozzle 26 to have independent suction power, a separate pump 38 is provided for each nozzle 26. In the robotic system 10 illustrated in FIG. 1, there are four pumps 38, one for each nozzle 26, such that each nozzle 26 has its own independent suction power independent of the other nozzles 26.

The horizontal member 32 of the robotic arm 30 is comprised of an actuator housing 48 containing a Y-axis actuator 40 and two Z-axis actuators 44, 46 contained within the actuator housing 48. The internal components of the Y-axis actuator 40 are described later and illustrated in FIG. 13 of this application. The Y-axis actuator 40 is coupled with the actuator housing 48 and moves along the frame 12. The robotic arm 30 is coupled to the Y-axis actuator 40. The Y-axis actuator 40 moves the robotic arm 30 and the end effector 22 back and forth in the Y-axis direction of movement as indicated by Y-axis arrow 42 to control placement of the nozzle tips 28 in the desired position in the Y-axis.

The actuator housing 48 also contains two Z-axis actuators—the $Z_1$-axis actuator 44 and $Z_2$-axis actuator 46. The internal components of the $Z_1$-axis actuator 44 and the $Z_2$-axis actuator 46 are described later and illustrated in FIG. 12 of this application. The actuator housing 48 contains a vertical rail 49A to allow the robotic arm 30 to move up and down the housing 48 in the Z-axis direction of movement as indicated by the Z-axis arrow 47. The $Z_1$-axis actuator 44 is coupled to the robotic arm 30, and the control system controls the $Z_1$-axis actuator 44 to control placement of the nozzle tips 28 in the desired position in the Z-axis. The rail 49A extends from the top of the housing 48 near the top 17 to the bottom of the housing 48 near the base 16 so that the robotic arm 30 can be moved up and down in the Z-axis. Note that the actuator housing 48 also contains a second vertical rail 49B that is located parallel to vertical rail 49A for the $Z_1$-axis actuator 44. This second vertical rail 49B is used to control an optional gripper arm described below and illustrated in FIG. 2.

The robotic system 10 illustrated in FIG. 1 also contains a plurality of shelves 50, also called trays, that hold targets 52 either containing fluid to be transported, or used to store transported fluid. In the example of the robotic system 10 illustrated in FIG. 1, two shelves 50A, 50C are illustrated. The bottom shelf 50C is the only shelf that is illustrated as containing targets 52. However, all of the shelves 50 are designed to hold targets 52, and the absence of targets 52 on the top shelf 50A is merely to illustrated components of the shelf 50 that would otherwise not be visible if the targets 52 on the shelf 50A were illustrated in FIG. 1. Also, please note that the robotic system 10 illustrated in FIG. 1 is designed to provide four shelves 50 each containing targets 52; however, two of the shelves 50 are not included in FIG. 1 so that components of the robotic system 10 in FIG. 1 to be described are not blocked from view.

The frame 12 of the robotic system 10 contains an inside wall 57, which is the inside of one of the sides 14 of the robotic system 10. Along this inside wall 57 are linear bearings 54, each comprised of a rail 56 and a rail guide 58. Each of the shelves 50 is attached to the rail 56 via the rail guide 58 such that the shelves are movable along the rail 56 by a corresponding X-axis actuator 60A, 60C (under control of the control system) in the X-axis direction of movement as indicated by the X-axis arrow 62. The X-axis actuator 60A, 60C causes the shelf 50 to move in a direction of the X-axis arrow 62 to align the targets 52 underneath the desired nozzles tips 28 of the end effector 22. The internal components of the X-axis actuator 60 is described later and illustrated in FIG. 11 of this application. Note that a separate X-axis actuator 60A, 60C is provided for each shelf 50A, 50C, respectively, so that each shelf 50A, 50C is independently controllable to move in the X-axis. In the illustration in FIG. 1, since there are two shelves 50 illustrated, two X-axis actuators 60A, 60C are indicated—one for each shelf 50. The present invention contemplates a separate X-axis actuator 60 for each shelf 50.

Since the X-axis actuator 60 can control the shelf 50 to move to any position to align the desired target 52 with the desired nozzle tip 28, the robotic system 10 does not require that the number of nozzle tips 28 be equal to the number of targets 52 to accomplish fluid transfer. This is because the shelf 50 containing the targets 52 can be moved in the X-axis via the X-axis actuator 60 to align any column of the targets 52 with any nozzle tip 26. If the X-axis actuator 60 could not control the shelf 50 to any position in the X-axis, but instead could only move the shelf 50 outward in the X-axis to a second position, the end effector 22 would either have to be controllable in all three axes of motion or would have to provide a nozzle tip 28 for each target 52 if the robotic arm 30 only moves in two axes of direction—the Y-axis and the Z-axis in the example illustrated in FIG. 1.

In summary, the control system of the robotic system 10 transports fluid by causing the nozzle tips 28 to align with the desired targets 52 in three axes of motion by (1) causing the X-axis actuator 60 to move the shelf 50 containing the targets to be aligned in the X-axis; and (2) causing the Y-axis actuator 40 and the $Z_1$-axis actuator 44 to move in the Y-axis and the Z-axis only, respectively, to align the nozzle tips 28 with the desired targets 52. In this manner, the robotic system 10 need not provide a third axis of movement to control the robotic arm 30 since the X-axis actuator 60 is capable of controllably moving the desired targets 52 underneath the nozzle tips 28 in the X-axis.

Note that in the robotic system 10 illustrated in FIG. 1, the shelves 50 are aligned vertically and stacked on top of each other so that a greater number of targets 52 can be provided in the robotic system 10 for fluid transport. For example, if a shelf 50 can hold forty-eight targets 52, providing four shelves 50 will allow the robotic system 10 to handle one hundred ninety-two targets. Although the example of the robotic system 10 in FIG. 1 includes four linear bearings 54 to allow for four shelves 50 of targets 52, the robotic system 10 can provide any number of shelves 50, including more than four, to provide a robotic system 10 to handle as many targets 52 as desired. If more shelves 50 are included in the robotic system 10 for fluid transport, the height of the robotic system 10 is increased to accommodate more shelves 50.

Note that the robotic system 10 illustrated in FIG. 1 conserves footprint size (i.e. the size of the base 16) by providing targets 52 on the shelves vertically stacked on top of each other. Also, note that the footprint size of the robotic system 10 will not increase in any direction if more shelves 50 containing targets 52 are added vertically upward. If it is desired to increase the target 52 handling capacity of the robotic system 10, only more shelves 50 need be added, which can be accomplished by only increasing the height of the robotic system 10. These aspects of the present invention are important, particularly in manufacturing and laboratory environments, where it is desirable to provide a robotic system that handles a larger number of targets with a minimum footprint size.

The shelves 50 in the example illustrated in FIG. 1 each contain two separate platforms 64A, 64B for holding two containers 68 of targets 52. In the example illustrated in FIG. 1, the targets 52 are comprised of a plurality of glass tubes 70 for holding fluid. The containers 68 provide for the tubes 70 to be organized in columns with the first column being designated as "71". Two platforms 64A, 64B are provided on each shelf 50 so that two containers 68, typically having a standard size, can be handled for greater target 52 handling capability. However, the present invention is not limited to two platforms 64A, 64B per shelf 50, and the shelf 50 could include room for only one platform 64 or more than two platforms 64. In order to place the container 68 in the proper position on the shelf 50 such that the X-axis actuator 60 can properly align the desired target 52 with the nozzle tip 28, limiters 66 are provided on two sides of the shelves 50 so that the containers 68 must be placed in a predetermined location. The containers 68 are designed to fit snugly in between the limiters 66 so that the platform 64 and thus the targets 52 are in a known location to the control system with respect to the shelf 50. A more complete description of the shelf 50 and its components is described later and illustrated in FIG. 10.

In the example of the robotic system 10 illustrated in FIG. 1, a wash station 72 is also provided. The wash station 72 is attached atop a wash station platform 74. The wash station 72 contains a washing fluid (not shown) so that the robotic system 10 can wash off the nozzle tips 28 if such is necessary to prevent contamination during a subsequent fluid transfer. An example where washing may be needed is in the transport of blood where blood in different tubes 70 representing different persons cannot be mixed together. In order to wash the nozzle tips 28, the robotic system 10 causes the Y-axis actuator 40 and the $Z_1$-axis actuator 44 to move the end effector 22 in Y-axis and downward in the Z-axis such that the nozzle tips 28 are placed inside the wash station 72. Note that since wash station 72 is in a stationary position and is below all of the shelves 50 near the base 16, it is not necessary to provide an actuator to move the wash station 72.

The robotic system 10 illustrated in FIG. 1 may also contain a disposal container 76 for disposal of tips (not shown) after fluid transport is accomplished. The robotic system 10 may insert tips on the nozzle tips 28 prior to the nozzles tips 28 being inserted into a tube 70 for fluid transport to prevent contamination. The robotic system 10 can control the Y-axis actuator 40 and the $Z_1$-axis actuators 44 to move the end effector 22 in Y-axis and downward in the Z-axis such that the nozzle tips 28 are located above the container 74 for disposal of tips. The base 16 of the robotic system 10 may also be configured to allow for convenient storage underneath the lowest rail 56 for storage of fluid containers 78 that contain fluid needed for operation of the robotic system 10.

Figure 2:
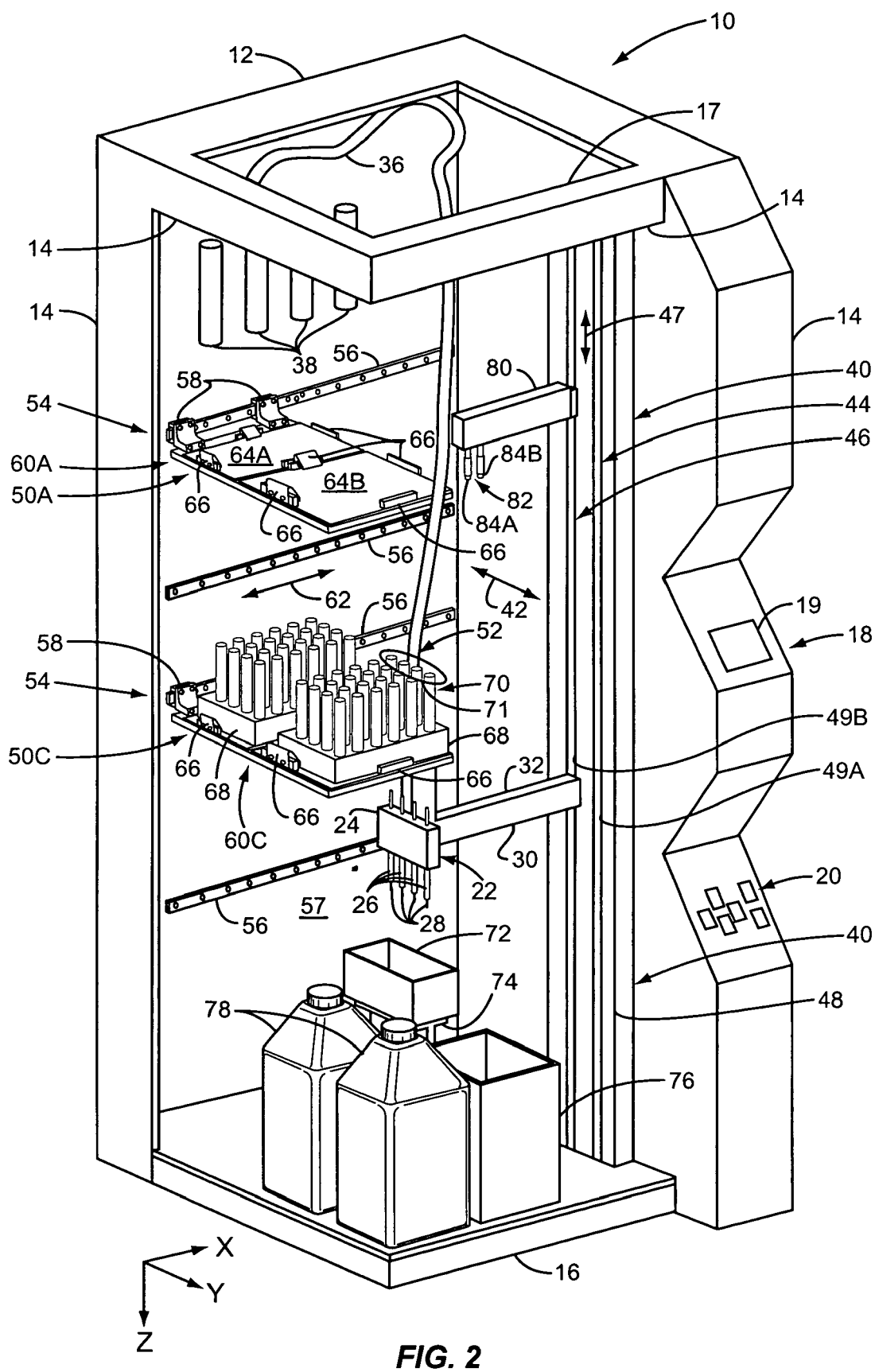
FIG. 2 illustrates a gripper arm for the robotic system used to grab and move targets provided on the trays.

FIG. 2 illustrates the robotic system 10 of FIG. 1, but also illustrates an optional second robotic arm called a "gripper arm" 80 that is connected to the vertical rail 49B, which is controlled by the $Z_2$-axis actuator 46. The gripper arm 80 contains tongs 82 that are comprised of a first finger 84A and a second finger 84B. The robotic system 10 controls the spacing between the two fingers 84A, 84B to grip a tube 70 for moving the tube 70. The robotic system 10 causes the gripper arm 80 to move in two axes of movement, the Y-axis and the Z-axis via the Y-axis actuator 40 and the $Z_2$-axis actuator 46, similar to the control of the robotic arm 30. The tube 70 to be gripped by the gripper arm 80 is controlled by movement of the shelf 50 containing the tube 70 via the X-axis actuator 60 in the X-axis direction just like that of the operation described above for FIG. 1. The only difference between the operation of the robotic arm 30 and the operation of the gripper arm 80 illustrated in FIG. 2 is that the gripper arm 80 is designed to only transport one tube 70 at a time, whereas the end effector 22 on the robotic arm 30 contains four nozzles 26 so that fluid can be transported from four tubes 70 at the same time.

Figure 3:
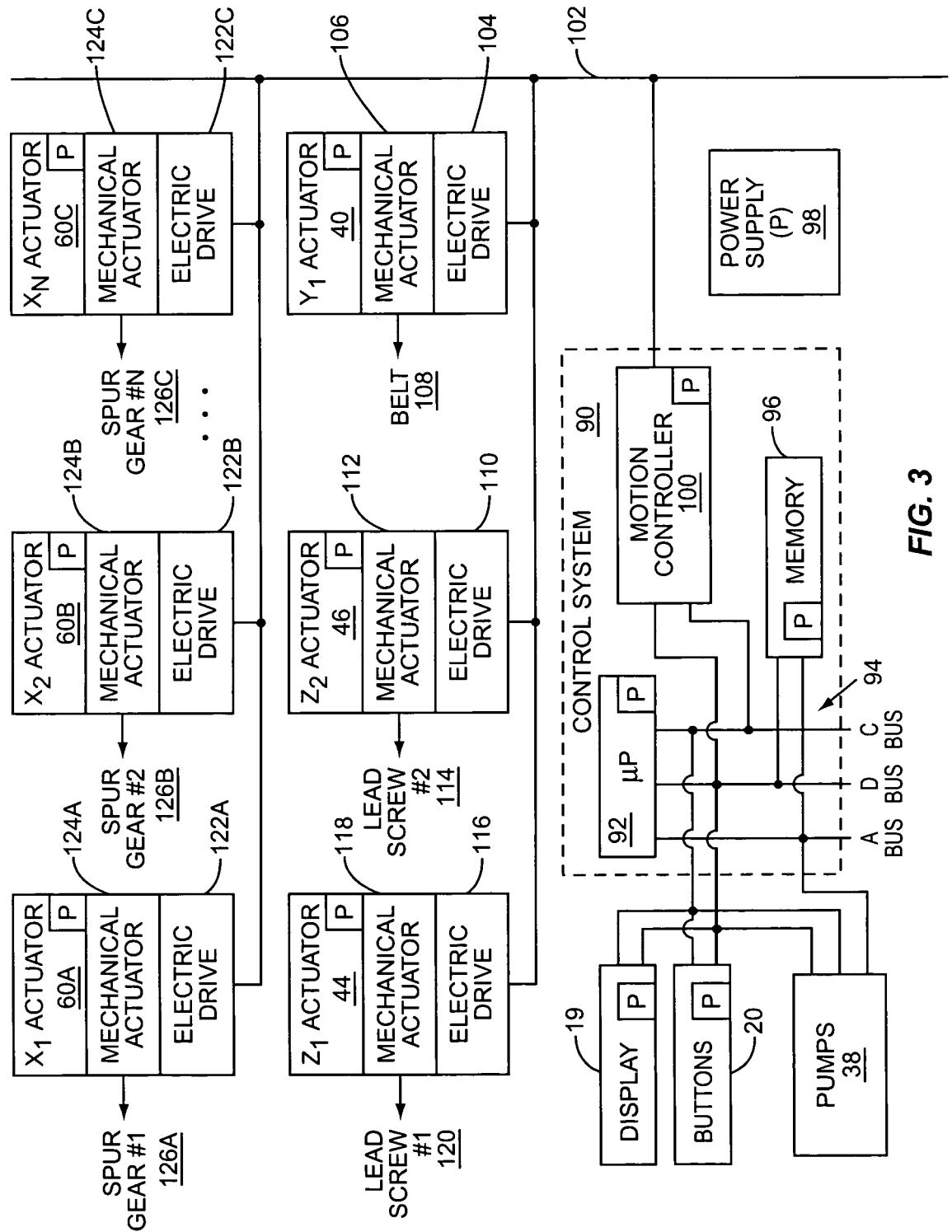
FIG. 3 illustrates a block diagram illustrating the hardware components of the robotic system.
Figure 5:
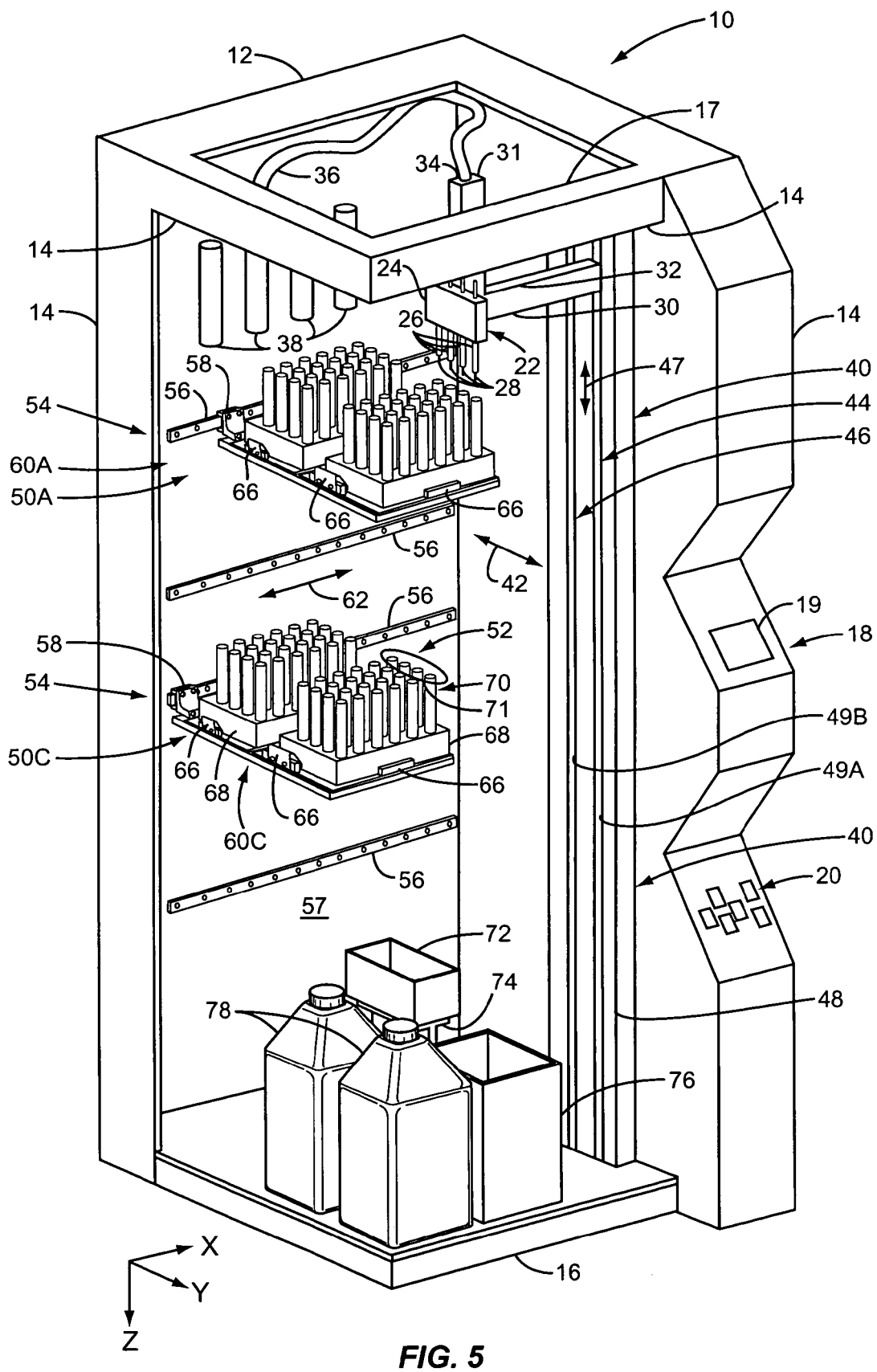
FIG. 5 illustrates the position of the robotic arm for table entry number 1 in the table illustrated in FIG. 4.

FIG. 3 illustrates a block diagram of a control system 90 within the robotic system 10 and the other hardware and software components that controls the movement and operation of the robotic arm 30 and nozzles 26, the gripper arm 80, and the shelves 50, via control of the $Y_1$-axis actuator 40, the $Z_1$-axis actuator 44, the $Z_2$ axis actuator 46, and the X-axis actuators 60A, 60B, 60C. The control system 90 is comprised of a microprocessor or microcontroller 92, memory 96, and a motion controller 100. The microprocessor 92 is coupled to the memory 96 and the motion controller 100 via an address, data and control bus 94, as is commonly known to one of ordinary skill in the art. The display 19 and the input keys 20 are also coupled to the control system bus 94 so that the display 19 is under control of the control system 90, and the microprocessor 92 can receive input from the input keys 20 indicating the operator's selections. The pumps 38 are also under control of the microprocessor 92 to control suction of the nozzles 26.

The memory 96 contains the control program used to execute the operation of the robotic system 10 and memory for data used by the control program. The microprocessor 92 may access and control the display 19, the input keys 20, and the motion controller 100 via input/output control or memory mapped input/output, depending on the type of microprocessor 92 and its architecture selected for use in the robotic system 10. A power supply 98 is provided in the robotic system 10 that provides power to each of the electrical components of the system. "P" indicators are included on the various components in FIG. 3 to illustrate components that are coupled to the power supply 98 for power.

The microprocessor 92 interfaces with the motion controller 100 to control the operation of the actuators 40, 44, 46, 60 for operation of the robotic system 10. A control line 102 is provided in order for the motion controller 100 to communicate to the actuators 40, 44, 46, 60 in the robotic system 10. Although only one control line 102 is illustrated in FIG. 3, the motion controller 100 communicates with each actuator 40, 44, 46, 60 over their own separate control line 102 coupled to the motion controller 102. However, as an alternative, the motion controller 100 could be configured to addressably access each of the components attached to communications bus individually so that only communications destined for a particular actuator 40, 44, 46, 60 are received by the intended actuator.

As illustrated in FIG. 3, X-axis actuators 60A, 60B, 60C are provided for each shelf 50, and each is coupled to the motion controller bus 102 so that each is controlled by the motion controller 100 under control of the microprocessor 92. The $X_1$-axis actuator 60A is a first actuator for a first shelf 50, the $X_2$-axis actuator 60B is for a second shelf 50, and the $X_N$ axis actuator 60C is for an Nth shelf 50. The illustration in FIG. 3 is intended to show that there is a dedicated X-axis actuator 60 for each shelf 50 to control movement of each shelf 50 independently in the X-axis. Each X-axis actuator 60A, 60B, 60C contains an electric drive 122A, 122B, 122C that is coupled to the motion controller bus 102. The electric drive 122A, 122B, 122C is designed to receive instructions from the motion controller 100 over the motion controller bus 102 to provide instructions to a mechanical actuator 124A, 124B, 124C. The mechanical actuator 124A, 124B, 124C converts the instructions from the electric drive 122A, 122B, 122C into mechanical energy to rotate a spur gear 126A, 126B, 126C in either the clockwise or counterclockwise direction to move the desired shelf 50 in the X-axis as desired. The spur gear 126A, 126B, 126C and how rotation of the spur gear 126A, 126B, 126C moves a shelf 50 is illustrated and discussed later below in FIG. 11.

The $Y_1$-axis actuator 40 is also coupled to the the motion controller 100 via a control line 102, which is under control of the microprocessor 92. The motion controller 100 communicates with the $Y_1$-axis actuator 40 via its electric drive 104. The electric drive 104 sends electrical signals to the mechanical actuator 106 to convert instructions from motion controller 100 into mechanical energy to control rotation of an actuator connected to a belt 108. The rotation of the belt 108 causes the actuator housing 48 to move in the Y-axis. More information about the belt 108 and its operation as the $Y_1$-axis actuator 40 to move the actuator housing 48 in the Y-axis is described below later and illustrated in FIG. 13 of this application.

The $Z_1$ axis actuator 44 and the $Z_2$ axis actuator 46 are also controlled by the motion controller 100 via coupling of their electric drives 116, 110 to the motion controller bus 102. Signals received by the electric drives 116, 110 from the motion controller 100 via the motion controller bus 102 are converted into mechanical energy via the mechanical actuators 118, 112 to rotate lead screw #1 120 in the $Z_1$-axis actuator 44 and lead screw #2 114 in the $Z_2$-axis actuator 46. Rotation of the lead screws 120, 114 cause the robotic arm 30 and gripper arm 80, respectively, to move up and down in the Z-axis. More information about the $Z_1$-axis actuator 44 and $Z_2$-axis actuator 46 and their control of lead screws #1 and #2 120, 114 to control the robotic arm 30 and the gripper arm 80 in the Z-axis is described later and illustrated in FIG. 12 in this application.

FIG. 4 illustrates a table showing an example of a fluid transfer performed by the robotic system 10. The table shows the positions of the X-axis actuators 60, the Y-axis actuator 40, and the $Z_1$ and the $Z_2$ axis actuators 44, 46 as controlled by the control system 90, for a fluid transport operation as an example. The columns in the table illustrated in FIG. 4 show the positions of each of the actuators 40, 44, 46, 60 of the robotic system 10. The rows indicate the sequential steps and positions of the actuators 40, 44, 46, 60 to accomplish fluid transport in accordance with the example to be described. FIGS. 5 through 9 illustrate how the robotic system 10 would appear during some of the steps contained in the rows of the table illustrated in FIG. 4 to illustrate the fluid transport example. In this example, the gripper arm 80 will not be controlled, and thus the $Z_2$-axis actuator 46 will not be moved by the control system 90.

As illustrated in FIG. 4, at the beginning of a fluid transport, the zero row, indicated as "HOME," shows each of the axis actuators $X_1$, $X_2$, $X_3$, $X_4$, $Y_1$, $Z_1$, and $Z_2$ 60A, 60B, 60C, 60D, 40, 44, 46 in the zero position. The control system 90 designates the "0" position as the shelves 50 being to their farthest left, the actuator housing 48 being closest to the inside wall 57, and robotic arm 30 and the gripper arm 80 being all the way up closest to the top 17. Four X-axis actuators 60A, 60B, 60C, 60D are shown in the table in FIG. 4—one X-axis actuator per shelf 50. Although four shelves 50 are not shown in FIG. 1, four rails 56 are provided in FIG. 1 for up to four shelves 50 to be provided. The Y column shows the location of the Y-axis actuator 40 that controls actuator housing 48 in the Y-axis thereby controlling movement of the robotic arm 30 and the gripper arm in the Y-axis. The $Z_1$ and $Z_2$ columns show the locations of the $Z_1$-axis actuator 44 and the $Z_2$-axis actuator 46 that control the movement of the robotic arm 30 and the gripper arm 80, individually and respectively, in the Z-axis.

According to the example illustrated in the table in FIG. 4, it is desirable to transport liquid from the tubes 70 in the first column 71 on the first shelf, indicated as shelf $X_1$ 50A, on platform 64B to the tubes 70 in the first column 71 on platform 64B on shelf 3, indicated as shelf $X_3$ 50C, located two shelves below shelf $X_1$ 50A. As illustrated in row 1 in the table in FIG. 4, the first step that the control system 90 must undertake is to position the nozzle tips 28 over top the tubes 70 in the first column of shelf $X_1$ 50A on platform 64B. This is accomplished by the microprocessor 92 instructing the motion controller 100 to cause the $X_1$-axis actuator 60A to move shelf $X_1$ 50A outward in the X-axis to position 50. This is illustrated in the robotic system 10 in FIG. 5 wherein shelf $X_1$ 50A is moved to the right from its leftward resting position. The microprocessor 92 must also instruct the motion controller 100 to cause the $Y_1$-axis actuator 40 to move to position 100 and the $Z_1$-axis actuator 44 to move to position 20 to cause the nozzle tips 28 to reside just above the tube 70 in the first column 71 on shelf $X_1$ 50A.

Figure 6:
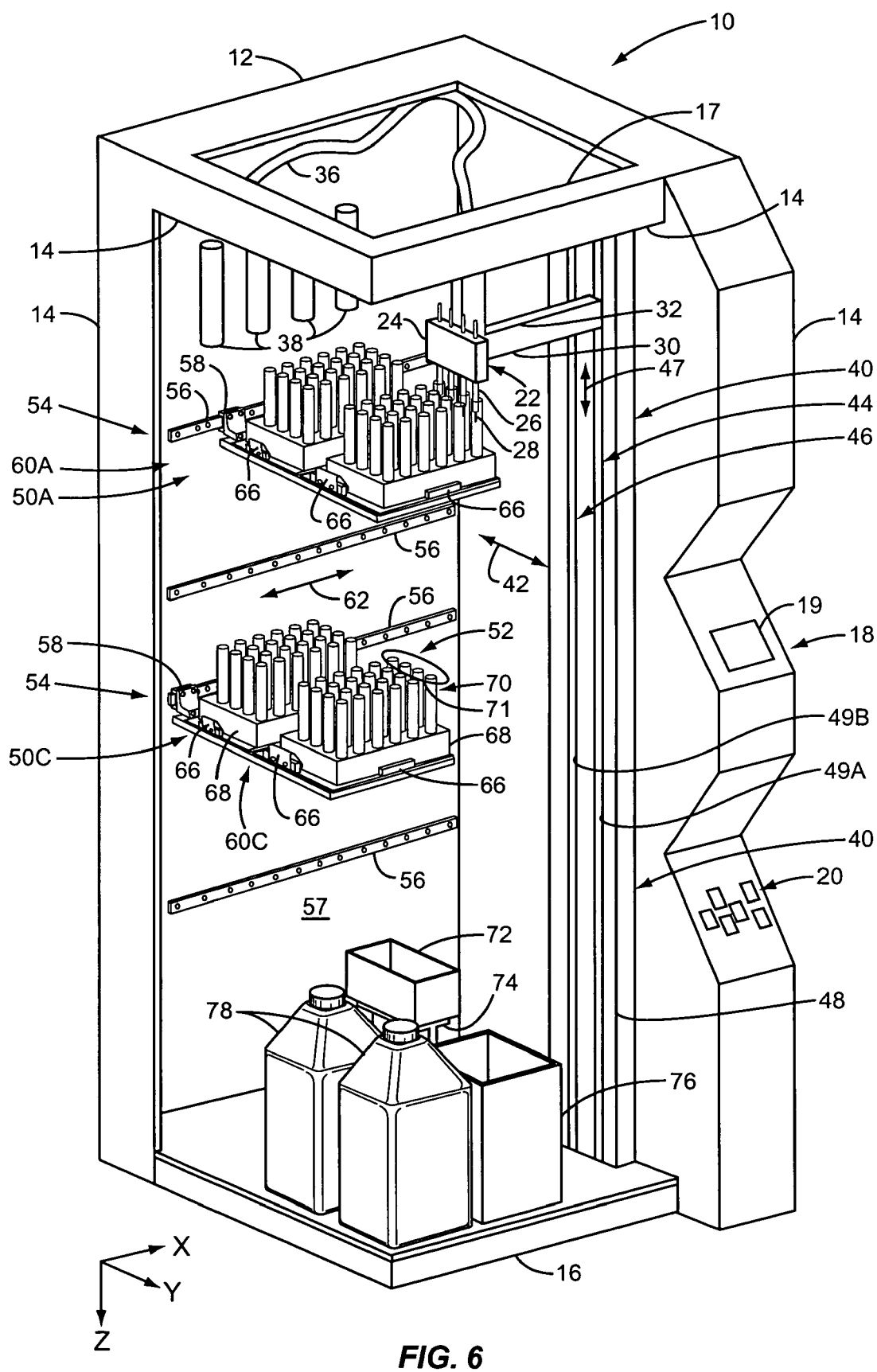
FIG. 6 illustrates the position of the robotic arm for table entry number 2 in the table illustrated in FIG. 4.

In row two in the table in FIG. 4, the microprocessor 92 next instructs the motion controller 100 to move the $Z_1$-axis actuator 44 to position 30, which causes the robotic arm 30 to move the end effector 22 downward causing the nozzle tips 28 to be inserted into the tubes 70 in the first column 71 of shelf $X_1$ 50A on platform 64B as illustrated in FIG. 6. The control system 100 can then activate the pumps 38 to create suction in the tubes 70 in which the nozzle tips 28 are inserted as illustrated in FIG. 6 to draw fluid out of the tubes 70.

Next, as illustrated in row 3 in the table illustrated in FIG. 4, the microprocessor 92 causes the motion controller 100 to cause the $Z_1$-axis actuator 44 to move back to position 20, the same position two steps prior in row 1, to cause the nozzle tips 28 to rise above the tubes 70. Next, as illustrated in row 4 in the table in FIG. 4, the microprocessor 92 instructs the motion controller 100 to move the $X_1$-axis actuator 60A back to position 0 so that the shelf $X_1$ 50A is moved leftward in the X-axis to its initial position. At this point, the nozzles 26 contain fluid from the tubes 70 in column 1 of shelf $X_1$ 50A on platform 64B.

Figure 7:
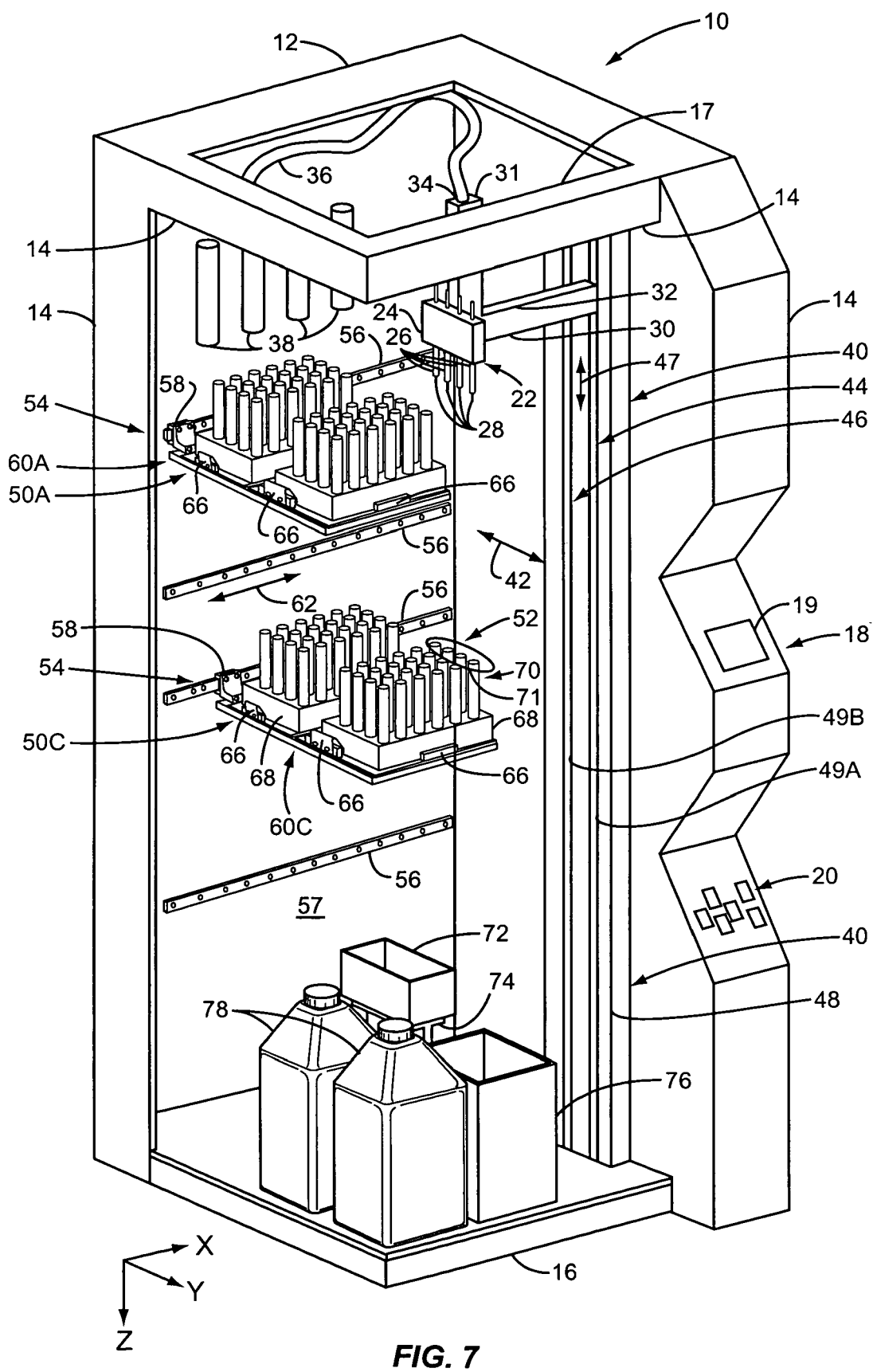
FIG. 7 illustrates the position of the robotic arm for table entry number 5 in the table illustrated in FIG. 4.

Next, as illustrated in row 5 in the table in FIG. 4, the microprocessor 92 instructs the motion controller 100 to cause the $X_3$-axis actuator 60C to move shelf $X_3$ 50C outward to the right in the X-axis so that the fluid contained in the nozzles 26 at this point can be transported to the tubes 70 in the first column 71 on shelf $X_3$ 50C on platform 64B as illustrated in FIG. 7. This is accomplished by the microprocessor 92 instructing the motion controller 100 to control the $X_3$-axis actuator 60C to move the shelf $X_3$ 50C to position 50.

Figure 8:
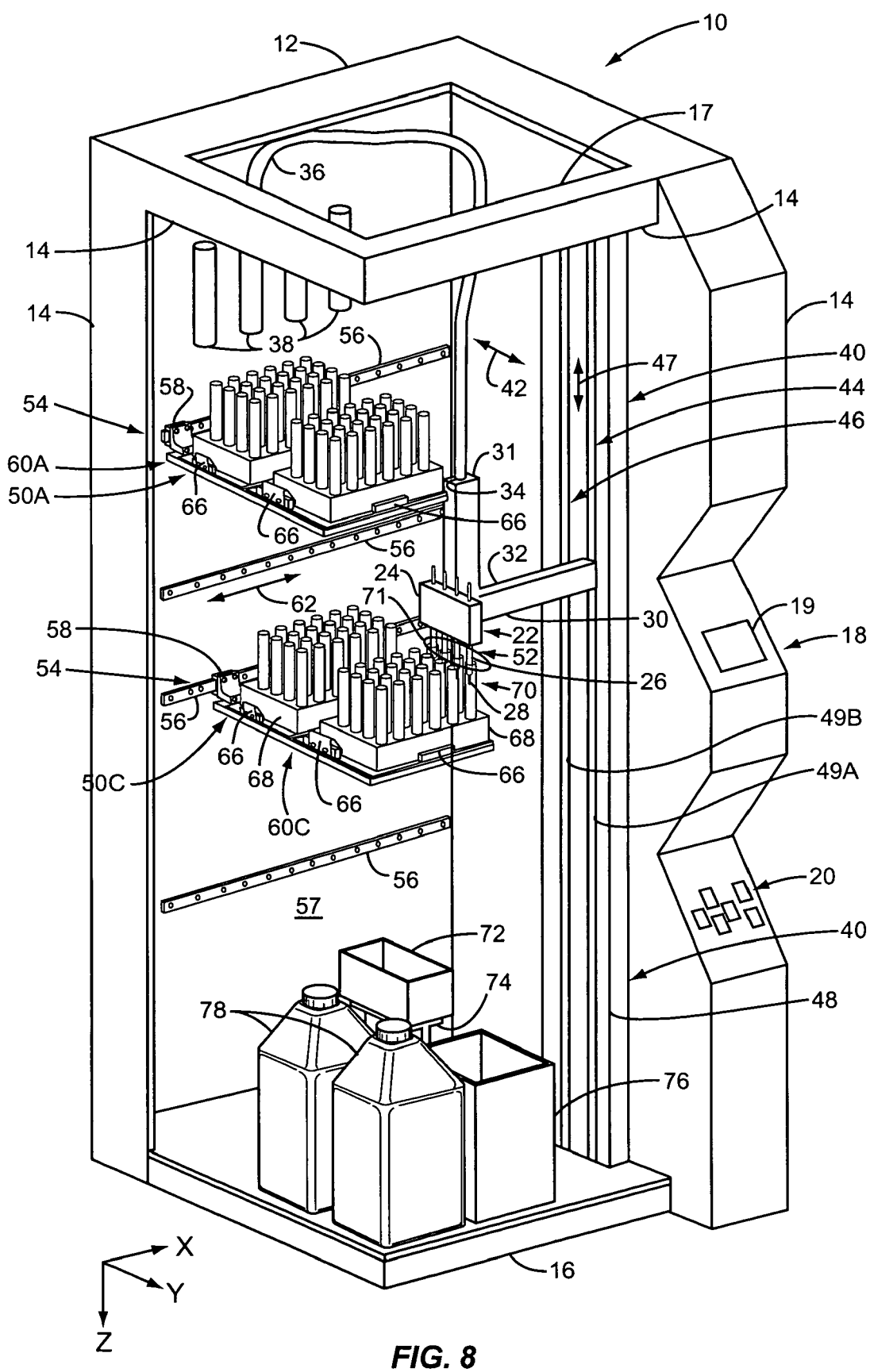
FIG. 8 illustrates the position of the robotic arm for table entry number 6 in the table illustrated in FIG. 4.

Next, as illustrated in row 6 in the table in FIG. 4, the microprocessor 92 instructs the motion controller 100 to move the $Z_1$-axis actuator 44 to position 310, which places the nozzle tips 28 inside the tubes 70 in first column 71 on shelf $X_3$ 50C on platform 64B as illustrated in FIG. 8. At this point, the fluid contained in the nozzles 26 is released into the tubes 70 by the microprocessor 92, causing the pumps 38 to discharge fluid. The microcontroller 92 next instructs the motion controller 100, as illustrated in row 7 in the table in FIG. 4, to move the $Z_1$-axis actuator 44 back up to position 300 to remove the nozzle tips 28 from the tubes 70 in the first column 71 to reside directly above the tubes 70 in the first column 71 so that the shelf $X_3$ 50C can be moved back to the left to its resting position without damaging the tubes 70.

Figure 9:
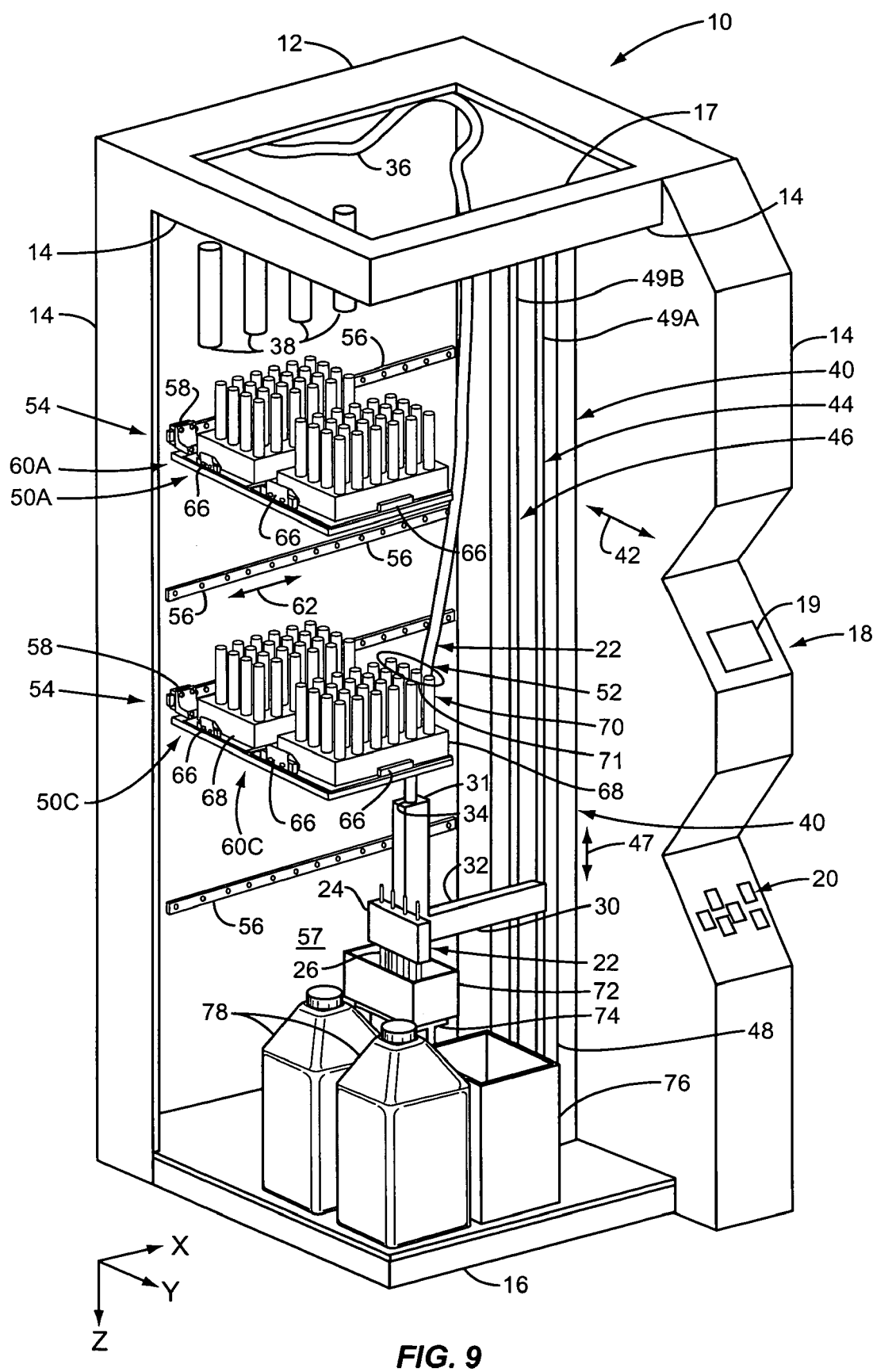
FIG. 9 illustrates the position of the robotic arm for table entry number 9 in the table illustrated in FIG. 4.

Next, as illustrated in row 8 in the table in FIG. 4, the microprocessor 92 instructs the motion controller 100 to move the $X_3$-axis actuator 60C back to position 0 to move shelf $X_3$ 50C left to its initial position. At this point in the example illustrated in FIG. 4, it is desired to wash the nozzle tips 28 in the wash station 72. As illustrated in row 9 in the table in FIG. 4, the microprocessor 92 instructs the motion controller 100 to move the $Y_1$-axis actuator 40 to position 32 and the $Z_1$-axis actuator 44 to position 415 downward so that the nozzle tips 28 are inserted into the wash station 72 as illustrated in FIG. 9. Thereafter, after the nozzle tips 28 have been washed in the wash station 72, the microprocessor 92 instructs the motion controller 100 to move the $Z_1$-axis actuator 44 to move the robotic arm 30 all the way upward to the 0 position in the Z-axis so that the end effector 22 is out of the way of the shelves 50 for the next fluid transport operation since one of the shelves 50 will have to be moved in the X-axis direction to the right during a subsequent transfer, which would interfere with the end effector 22 if the end effector 22 was left in position 415 all the way down in the wash station 72.

In summary, in the fluid transfer example illustrated in the table in FIG. 4, the control system 90 of the robotic system 10 has been programmed to move fluid from shelf $X_1$ 50A to shelf $X_3$ 50C wherein the fluid in tubes 70 in the first column 71 of shelf $X_1$ 50A is transported to the tubes 70 in the corresponding first column on shelf $X_3$ 50C. The control system 100 will also continue to transport fluid between tubes 70 on shelf $X_1$ 50A to shelf $X_3$ 50C by transporting fluid from tubes 70 in the second column of shelf $X_1$ 50A to tubes 70 in the corresponding second column on shelf $X_3$ 50C, and so forth, such that fluid from each of the columns of shelf $X_1$ 50A are transported to their corresponding columns in shelf $X_3$ 50C. In row 11 in the table in FIG. 4, the operation performed in rows 1 through 10 is repeated, except that an adder $C_1$ is added to the position of the $X_1$-axis actuator 60A when it is moved to a position other than 0, and an adder $C_1$ is added to the $X_3$-axis actuator 60C to a position other than 0, so that the $X_1$ shelf 50A and the $X_3$ shelf 50C move in the X-axis direction of movement such that the nozzle tips 28 are aligned with the tubes 70 in column 2. Adder $C_1$ corresponds with a position distance between columns in the container 68. Since the container 68 is of a uniform type guaranteeing that the spacing between the columns of tubes 70 are the same, the movements in steps 1 through 10 can be repeated to transport liquids for subsequent columns in the container 68.

Figure 10:
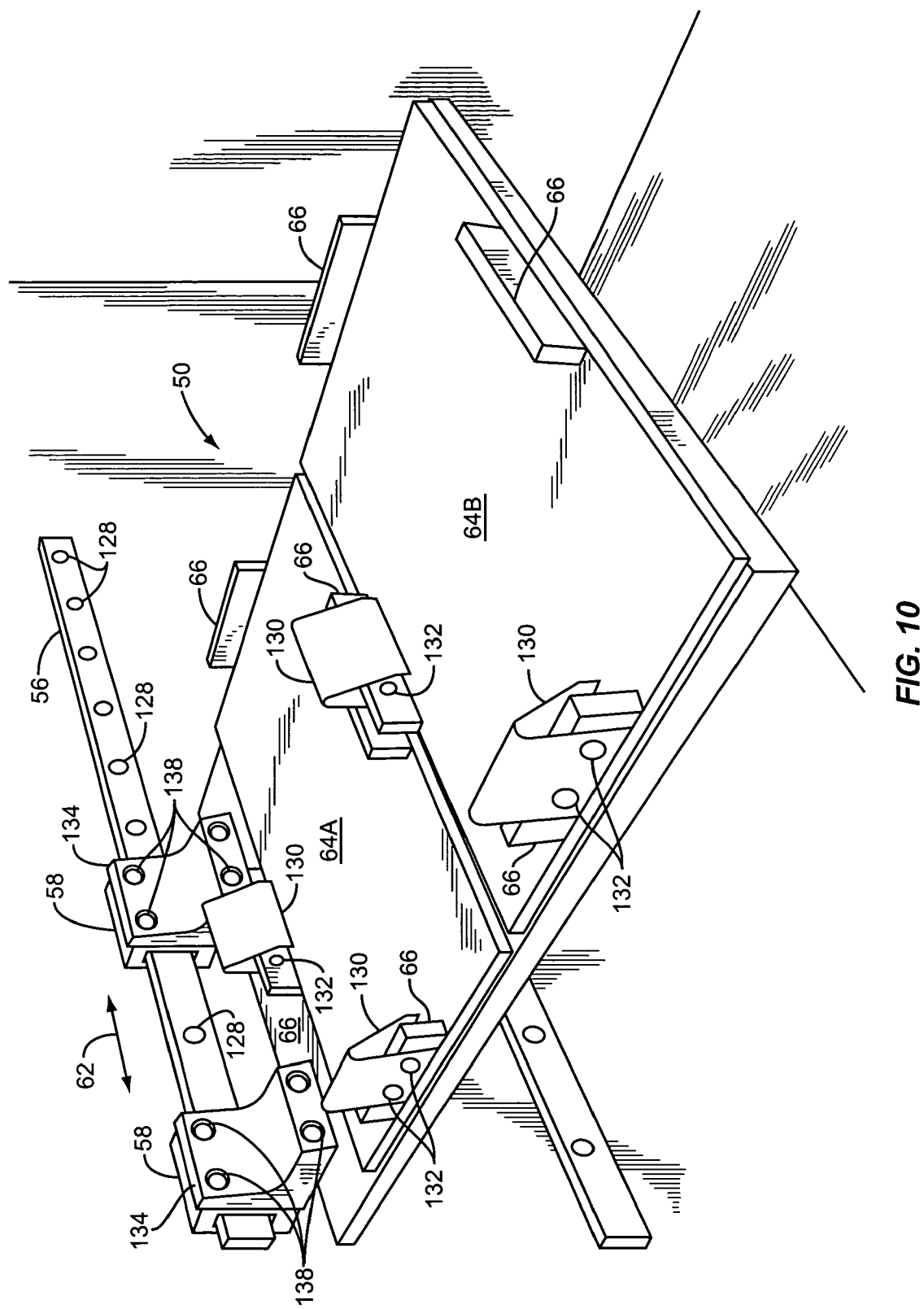
FIG. 10 illustrates a more detailed view of the tray that holds the targets.

FIG. 10 illustrates a more detailed view of the shelf 50 and the linear bearing 54 as previously described and illustrated in FIG. 1. The rail 56 is attached to the inside wall 57 of the frame 12 via fasteners 128. The limiters 66 each contain a flexible, resilient flange 130 that may be constructed out of a thin metal sheeting so that platforms 68 placed on the shelf 50 can be snugly fit on the platforms 64A, 64B to bias the containers 68 towards the limiters 66 that do not contain flanges 130. Note that only two limiters 66 contain the flange 130 to secure the platform 68 snugly against the other two limiters 66 that do not contain a flange 130 in the example illustrated. The flange 130 is connected to the limiters 66 via fasteners 132.

The shelf 50 is attached to the rail 56 to create a linear bearing 54 via bracket 134 and rail guide 58. The rail guide 58 is in the shape of a C-clamp. Two brackets 134 are attached to shelf 50 via fasteners 138. The bracket 134 is a right-angle bracket wherein the other side of the bracket 134 is attached to a rail guide 136 via fasteners 138. The rail guide 58 is constrained to the rail 56 to allow movement along the rail 56 in the X-axis as indicated by the X-axis arrow 62.

Figure 11:
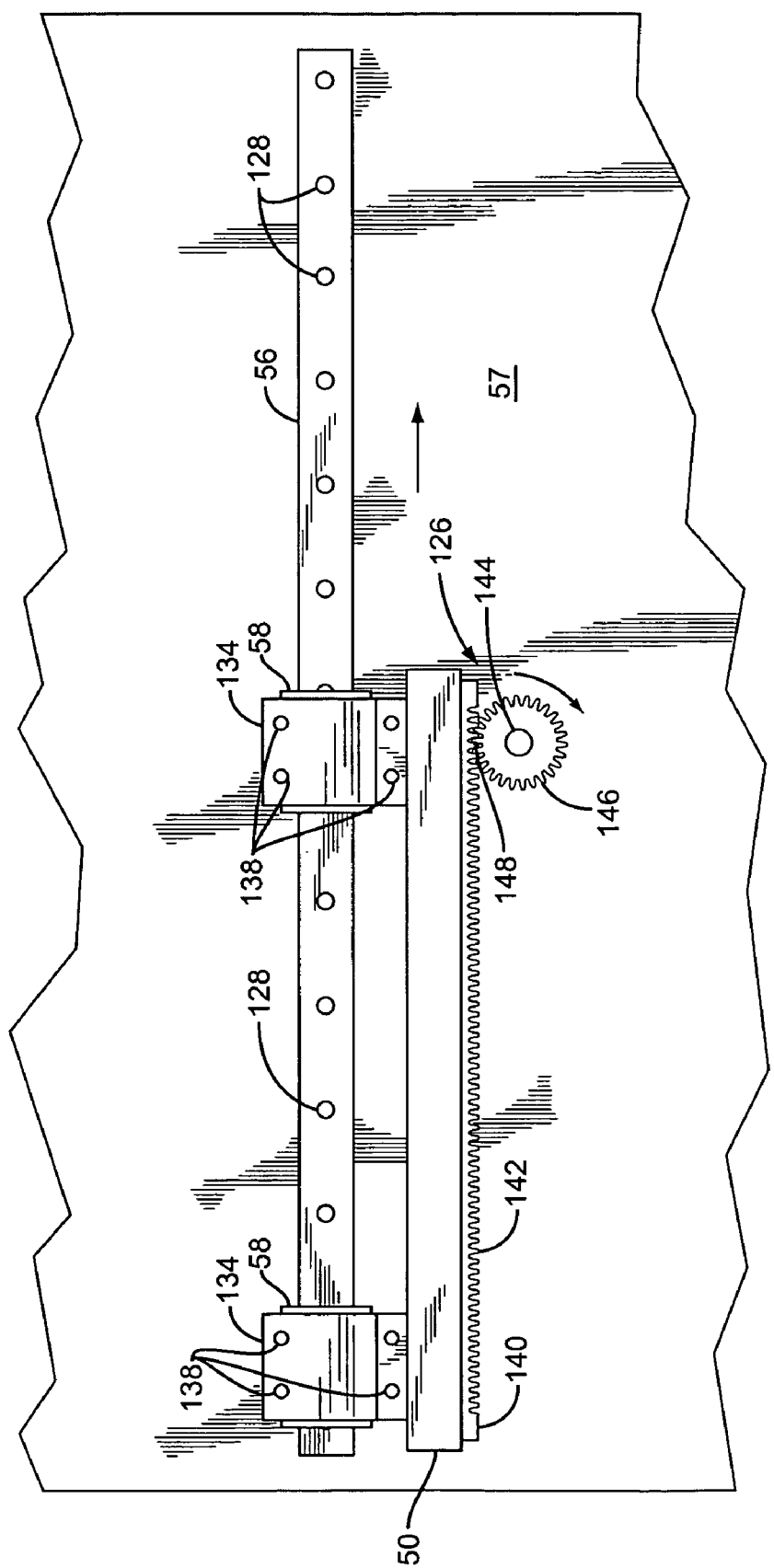
FIG. 11 illustrates the X-axis actuator used to move the tray containing the targets in the X-axis.

FIG. 11 illustrates an example of the X-axis actuator 60 that causes the shelf 50 to move in the X-axis direction along rail 56. Underneath each shelf 50 is contained a gear rack 140 that contains a series of teeth 142 along its edge. A shaft 144 extends through the inside wall 57 and is coupled to the spur gear 126. The shaft 144 is coupled to a rotation mechanical actuator 124 (not shown) that is located on the backside of the frame 12. The spur gear 126 has teeth 146 that interlock with the teeth of gear rack 140 at a point of locking 148. The microcontroller 92 causes the shelf 50 to move in the X-axis direction by controlling the mechanical actuator 124 to rotate the shaft 144 thereby rotating the spur gear 126 in either the clockwise or counterclockwise direction and engaging the teeth 142 on the gear rack 140 to move the shelf 50 along the rail 56. Note that although this is one example of an X-axis actuator 60 that can be used for the present invention, the present invention is not limited to this particular type of X-axis actuator and any type of actuator that is capable of moving shelf 50 in the X-axis direction may be used with the robotic system 10.

Figure 12:
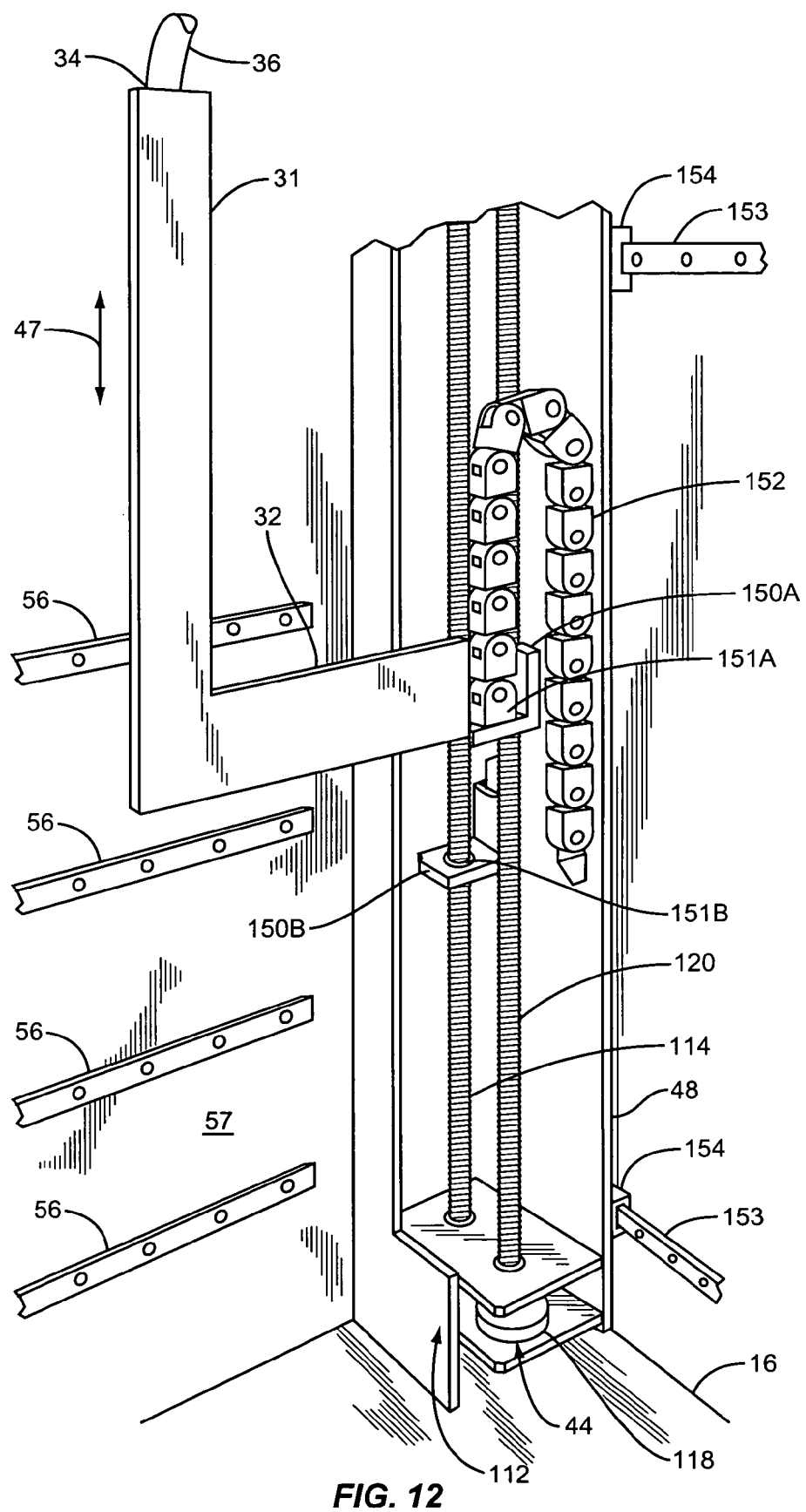
FIG. 12 illustrates the Z-axis actuator used to move the robotic arm and the gripper arm in the Z-axis.

FIG. 12 illustrates an example of the $Z_1$ and $Z_2$-axis actuators 44, 46 that causes the robotic arm 30 and the gripper arm 80 to move up and down in the Z-axis direction. The gripper arm 80 is not illustrated in FIG. 12, but the lead screw #2 114 that is rotated to move the gripper arm 80 up and down in the Z-axis direction is illustrated. The description of the $Z_1$-axis actuator 44 to move the robotic arm 30 is equally applicable to the $Z_2$-axis actuator 46 to move the gripper arm 80.

The $Z_1$-axis actuator 44 is comprised of a mechanical actuator 118 that rotates in the clockwise and counterclockwise direction to rotate. The mechanical actuator 118 is coupled to lead screw #1 120 so that the lead screw #1 120 rotates when the mechanical actuator 118 is directed by the motion controller 100 to rotate. The robotic arm 30 is coupled to the lead screw #1 120 via a bracket 150A. The bracket 150A contains a threaded orifice 151A that receives the lead screw #1 120 which extends therethrough. The robotic arm 30 is attached to the bracket 150A so that when the mechanical actuator 118 rotates to rotate lead screw #1 120, the bracket 150A moves on the lead screw #1 120, which in turn causes the robotic arm 30 to move in conjunction with the bracket 150A in the Z-axis.

A wiring conduit 152 is provided to house wiring that provides power and control lines to the nozzles 26. The wiring is described and illustrated in FIG. 13 below. The wiring conduit 152 is flexible and prevents the wiring inside from being damaged as the robotic arm 30 is moved up and down under control of the $Z_1$-axis actuator 144 in the Z-axis. Mechanical actuator 112 and bracket 150B are also provided for lead screw #2 114 that cause the gripper arm 80 to move up and down in the Z-axis like that of the robotic arm 30.

Note that although this is one example of a Z-axis actuator 44, 46 that can be used for the present invention, the present invention is not limited to this particular type of Z-axis actuator and any type of actuator that is capable of moving the robotic arm 30 and/or gripper arm 80 in the Z-axis direction may be used with the robotic system 10.

FIG. 12 also illustrates a linear bearing in the form of a rail guide 154 that is coupled to the rail 153 to move the actuator housing 48 in the Y-axis direction. A rail 153 and rail guide 154 are provided at the top and the bottom of the frame 12 to transport the actuator housing 48. The Y-axis actuator 140 is illustrated in FIG. 13, which causes the actuator housing 48 to move in the Y-axis direction to cause the robotic arm 30 and the gripper arm 80 to be controllably moved in the Y-axis by the control system 90.

Figure 13:
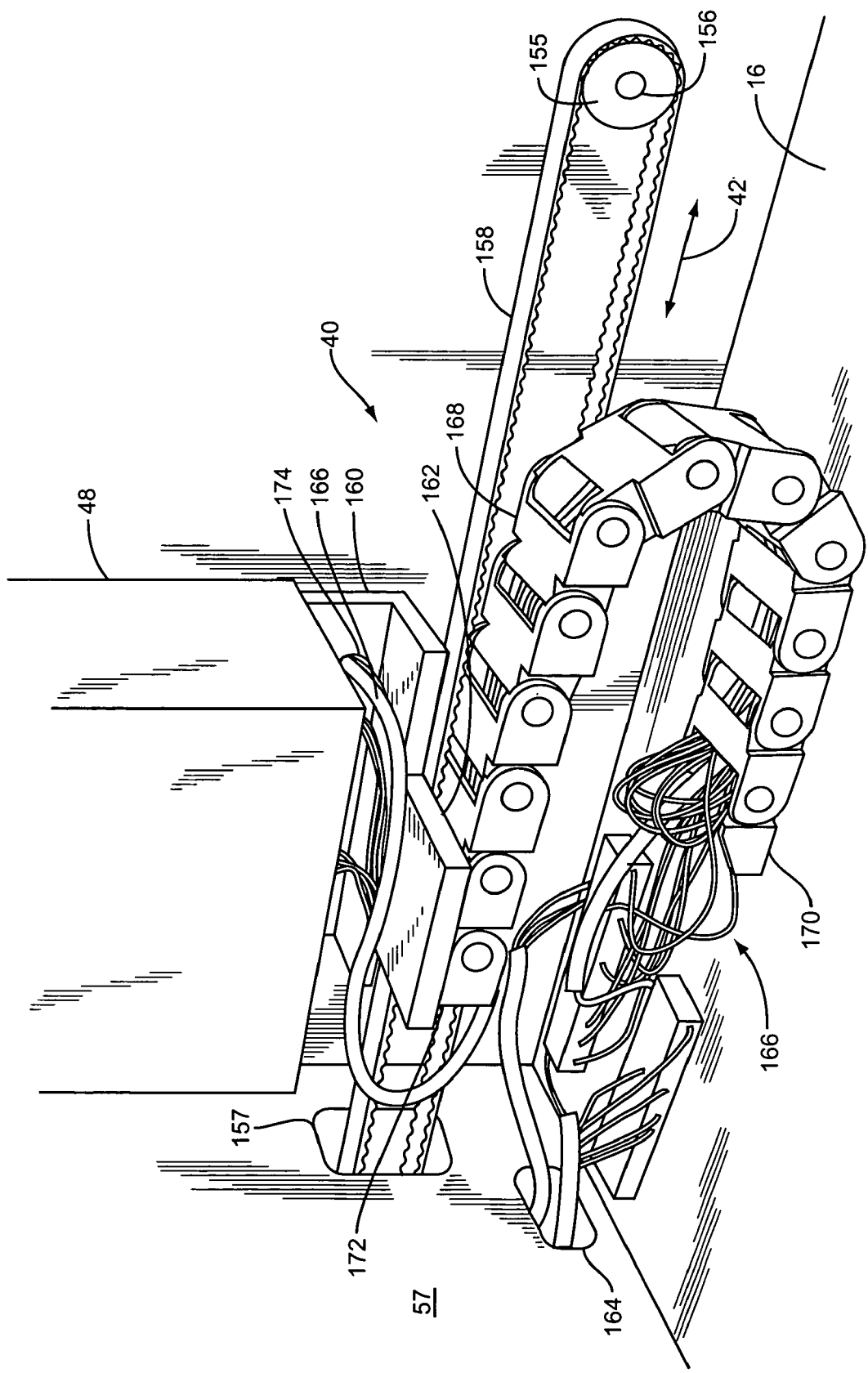
FIG. 13 illustrates the Y-axis actuator used to move the actuator housing to move the robotic arm and gripper arm in the Y-axis.

FIG. 13 illustrates the Y-axis actuator 40 that may be used with the robotic system 10 to move the actuator housing 48 in the Y-axis direction thereby providing Y-axis movement for the robotic arm 30 and the gripper arm 80, as previously describe above. A pulley 155 is provided that is attached to the frame 12 of the robotic system 10 via a shaft 156. A complementary mechanical actuator 106 in the form of a disc (not shown) is also provided on the rear side of the frame 12 on the other side of orifice 157. A belt 158 is placed tightly around the mechanical actuator 106 and the pulley. The control system 90 causes the mechanical actuator 106 to rotate in either a clockwise or counterclockwise direction thereby causing the belt 158 to move in response. The actuator housing 48 contains a bracket 160 that contains a platform 162 attached to the belt 158 such that when the belt 158 moves in the Y-axis direction, the belt 158 applies a force to the platform 162 to cause the actuator housing 148 to move along the rails 154 via the rail guide 153 (as previously illustrated in FIG. 12) in the Y-axis direction thereby providing Y-axis movement of the robotic arm 30 and the gripper arm 80.

An orifice 164 is provided in the inside wall 57 of the frame 12 to allow for wires 166 to extend from the rear side of the frame 12 through the inside wall 57 into the inside of the robotic system 10. The wires 166 provide power and control to the end effector housing 22 to provide control and power to the nozzles 26 for fluid transfer. The wires 166 are inserted into a flexible wiring conduit 168 that is affixed on one end 170 to the base 16 and affixed on the other end 172 to the platform 162 in order to contain the wires 166 and prevent the wires 166 from becoming damaged when the actuator housing 48 moves in the Y-axis. As the actuator housing 48 moves back and forth in the Y-axis direction, the wiring conduit 168 as attached to the platform 162 will move in turn and will bend at different points to protect the wires 166. The wires 166 exit from the other end 172 of the wiring conduit 168 and enter into the inside of the actuator housing 148 through an orifice 174.

Note that although FIG. 13 illustrates one example of a Y-axis actuator 40 that can be used for the present invention, the present invention is not limited to this particular type of Y-axis actuator and any type of actuator that is capable of moving actuator housing in the Y-axis direction may be used with the robotic system 10.

Those skilled in the art will recognize improvements and modifications to the preferred embodiments of the present invention. All such improvements and modifications are considered within the scope of the concepts disclosed herein and the claims that follow.

What is claimed is:

1. A robotic transfer system, comprising:
a control system;
a frame;
a plurality of first actuators attached to the frame;
a plurality of linear bearings attached to the frame wherein each of the plurality of linear bearings is controlled to be moveable to any position by one corresponding actuator in the plurality of first actuators only in a first axis of motion;
a plurality of shelves each containing a plurality of targets wherein each shelf in the plurality of shelves is attached to one corresponding bearing in the plurality of linear bearings and wherein each of said plurality of shelves is stacked in a vertical arrangement;
an arm attached to the frame and moveable only in two axes of motion both orthogonal to the first axis of motion, wherein the arm comprises:
a second actuator that moves only in one of the two axes of motion; and
a third actuator that moves only in the other of the two axes of motion; and
an end effector attached to the third actuator;
the control system electronically coupled to the plurality of first actuators and the second and third actuators, wherein the control system controls coupling the end effector to one of the plurality of targets by controlling an actuator in the plurality of first actuators corresponding to the shelf containing the one of the plurality of targets to independently move in the first axis of motion, and controlling the second and third actuators to move in the two axes of motion to align the end effector with the one of the plurality of targets, wherein said second and third actuators are not controllable to move in the first axis of motion.

2. The system of claim 1, wherein the end effector contains one or more nozzles for fluid transfer.

3. The system of claim 2, further comprising one or more pumps, wherein each of the one or more pumps is coupled individually to the one or more nozzles wherein the pump provides suction power to the nozzle for drawing in fluid.

4. The system of claim 1, wherein said plurality of targets comprises a plurality of glass tubes.

5. The system of claim 1, further comprising a wash station wherein said control system controls moving the end effector into the wash station by controlling the second and third actuators to move the end effector in two axes of motion.

6. The system of claim 1, wherein the plurality of targets on each shelf are contained in a container.

7. The system of claim 6, wherein the plurality of targets are arranged in the container in a row and column format.

8. The system of claim 6, wherein each of the plurality of shelves contains a plurality of platforms wherein each platform is designed to hold the container.

9. The system of claim 1, further comprising a user interface coupled to the control system for an operator to program the robotic system.

10. The system of claim 1, wherein the plurality of first actuators are each comprised of a mechanical actuator that rotates a spur gear wherein the spur gear is coupled to a gear rack attached to each of the plurality of shelves.

11. The system of claim 10, wherein the control system rotates the spur gear to move one of the plurality of shelves in the first axis of motion.

12. The system of claim 1, wherein the second actuator is comprised of an actuator housing attached to a belt wherein the control system causes a mechanical actuator coupled to the belt to rotate the belt thereby causing the actuator housing to move in the second axis of motion.

13. The system of claim 12, wherein the third actuator is comprised of a lead screw coupled to the end effector wherein the control system causes a mechanical actuator coupled to the lead screw to rotate the lead screw thereby causing the end effector to move in the third axis of motion.

14. A method of robotically transporting a material, comprising the steps of:
    selecting a target containing a material to transfer from a plurality of shelves containing a plurality of targets wherein each of the plurality of shelves are stacked in a vertical arrangement with respect to one another;
    moving a shelf containing the target from the plurality of shelves only in a first axis of motion by causing a first actuator coupled to the shelf to move the shelf in the first axis of motion to align an end effector with the target; and
    coupling the end effector with the target comprised of:
        moving an arm that is only moveable in two axes of motion both orthogonal to the first axis of motion, which is comprised of:
            instructing a second actuator to move the arm in a second axis of motion from the two axes of motion; and
            instructing a third actuator to move the arm in a third axis of motion from the two axes of motion in a different axis from the second axis of motion;
    wherein said second and third actuators are not controllable to move in the first axis of motion.

15. The method of claim 14, further comprising coupling a pump to the end effector to provide suction to the end effector when the end effector is coupled with the target.

16. The method of claim 14, further comprising moving the end effector into a wash station by:
    instructing a second actuator to move the arm in a second axis of motion from the two axes of motion to align end effector with the wash station in the second axis of motion; and
    instructing a third actuator to move the arm in a third axis of motion from the two axes of motion in a different axis from the second axis of motion to align the end effector with the wash station in the third axis of motion.

17. The method of claim 14, wherein the step of moving the shelf is comprised of rotating a spur gear wherein the spur gear is coupled to a gear rack attached to the shelf.

18. The method of claim 14, wherein the step of instructing a second actuator to move the arm in a second axis of motion from the two axes of motion comprises moving a belt wherein the belt is attached to the arm thereby causing the arm to move in the second axis of motion.

19. The method of claim 14, wherein the step of instructing a third actuator to move the arm in a third axis of motion from the two axes of motion in a different axis from the second axis of motion, wherein the third actuator is comprised of rotating a lead screw wherein the lead screw is coupled to the end effector thereby causing the end effector to move in the third axis of motion.

* * * * *